(12) United States Patent
Piana

(10) Patent No.: US 8,305,570 B2
(45) Date of Patent: Nov. 6, 2012

(54) METHOD AND DEVICE FOR DETERMINING A FOAM DENSITY

(75) Inventor: Stefan Piana, Köfering (DE)

(73) Assignee: Krones AG, Neutraubling (DE)

( * ) Notice: Subject to any disclaimer, the term of this patent is extended or adjusted under 35 U.S.C. 154(b) by 247 days.

(21) Appl. No.: 12/786,608

(22) Filed: May 25, 2010

(65) Prior Publication Data

US 2010/0302540 A1    Dec. 2, 2010

(30) Foreign Application Priority Data

May 26, 2009  (DE) .......................... 10 2009 022 691

(51) Int. Cl.
   *G01N 21/00*    (2006.01)
(52) U.S. Cl. ..................................... 356/239.6; 356/338
(58) Field of Classification Search ............... 356/239.6, 356/239.4, 240.1, 427, 336, 337, 338; 382/141, 382/142; 250/223 B; 73/60.11
   See application file for complete search history.

(56) References Cited

U.S. PATENT DOCUMENTS

| | | | | |
|---|---|---|---|---|
| 3,454,759 A | * | 7/1969 | Calhoun ..................... | 250/338.1 |
| 4,267,509 A | * | 5/1981 | Graham ....................... | 324/244.1 |
| 5,536,935 A | | 7/1996 | Klotzsch et al. | |
| 5,542,004 A | * | 7/1996 | Constant et al. .............. | 382/141 |
| 5,597,950 A | * | 1/1997 | Mullen ........................ | 73/60.11 |
| 5,864,600 A | * | 1/1999 | Gray et al. ....................... | 378/57 |
| 6,226,081 B1 | * | 5/2001 | Fantone et al. ............. | 356/239.6 |
| 2006/0210139 A1 | * | 9/2006 | Carroll et al. .................. | 382/141 |
| 2010/0201792 A1 | * | 8/2010 | Brinz et al. ..................... | 348/61 |

FOREIGN PATENT DOCUMENTS

| | | |
|---|---|---|
| DE | 102004054859 A1 | 5/2006 |
| DE | 102007004346 A1 | 7/2008 |
| EP | 0544428 A1 | 6/1993 |
| JP | 51133062 A | 11/1976 |
| JP | 53017765 A | 2/1978 |
| WO | WO 2005/003758 A1 | 1/2005 |
| WO | WO-2005003758 A1 | 1/2005 |

OTHER PUBLICATIONS

German Search Report for 102009022691.5 mailed Nov. 18, 2009.
European Search Report for 10163974.8 dated Dec. 5, 2011.
Japanese Office Action for Japanese Patent Application No. 2010-119378, mailed Jan. 17, 2012.

* cited by examiner

*Primary Examiner* — Hoa Pham

(74) *Attorney, Agent, or Firm* — Marshall, Gerstein & Borun LLP

(57) ABSTRACT

Method and device for determining a foam density of foam in beverage containers utilizing the Tyndall effect, and having a focused light bundle emitted into the foam by means of a light source, where the light bundle is refracted in the foam and a scattered ray becomes visible on a surface of the foam. Via a measurement of the contour of such a light spot, conclusions on the foam density can be drawn. For this, one or several lasers can be integrated into existing filling level measuring means which are coupled to the already existing measuring means.

16 Claims, 2 Drawing Sheets

METHOD AND DEVICE FOR DETERMINING A FOAM DENSITY

CROSS-REFERENCE TO RELATED APPLICATION

The present application claims the benefit of priority of German Application No. 102009022691.5, filed May 26, 2009. The entire text of the priority application is incorporated herein by reference in its entirety.

FIELD OF THE DISCLOSURE

The disclosure relates to a method for determining the foam density of foam according to the preamble of claim 1 as well as to a device for this according to the preamble of claim 5.

BACKGROUND

In beverage filling systems, a layer of foam is often formed during the filling in particular of beverages particularly containing carbon dioxide into beverage containers, such as bottles. Depending on the type of beverage, more or less foam can be formed. In particular during the filling of beer, a lot of foam is often formed. Normally, it takes some time until the foam has settled, i.e. until the liquid quantity bound in the foam is released. To check the liquid quantity in the beverage container, the filling level is measured. However, due to the forming foam, it is difficult, if not even impossible, to accurately determine the filling level directly after filling, because for doing so, one actually has to wait until the foam has settled. A determination of the liquid bound in the foam only on the basis of the dimensions of the foam often involves errors as the density of the forming foam varies, so that the bound liquid quantity does not only depend on the type of beverage but also varies from container to container.

If oxygen-sensitive beverages, such as beer, are filled, it is moreover common to inject a fine, sterile water jet into the filling orifice just in front of the closer (so-called HDE method). The foam generated in the process then displaces the oxygen still present above the filling level. To verify or check the correct function, it would also be desirable to know something about the foam density formed in the process.

With common methods, such as high frequency (HF), IR deflection, IR absorption, the liquid quantity in the foam cannot be determined. These methods have the disadvantage that they cannot detect different foam structures.

Though methods for measuring foam are known, one can only determine decomposition rates of the foams with these methods. In one of these methods, a light beam is emitted into the foam, where the light emerging from the foam on the opposite side is detected by a measuring device. The light beam and the measuring device rotate around the foam layer during the process. However, no exact determination of the foam density is possible with this method.

SUMMARY OF THE DISCLOSURE

It is therefore the object of the disclosure to suggest a method and a device by means of which the liquid quantity bound in the foam can be detected to calculate e.g. the filling level resulting after the foam has settled or to generally be able to observe foam formations.

A light beam is introduced into the foam forming immediately after the filling of the liquid into the container or the foam purposefully generated before the subsequent closing. This light beam penetrates the foam and is expanded in the process. To determine the foam density, the contour of a light spot generated by the light beam in the foam is determined, where the contour permits conclusions on the foam density.

The method here utilizes the effect that the foam brings about a scattering of the light beam. In the process, a differently high foam density causes a differently strong scattering, i.e. divergence of the beam. Highly dense foam which binds a high liquid quantity causes a strong scattering of the light beams. Reversely, the scattering is weaker if the foam binds less liquid, that means the foam is less dense.

The scattering of the light observed here is also referred to as Tyndall effect. This effect occurs if particles are suspended in a liquid or in a gas, where the size of the particles is comparable to the wave length of the light (ca. 100 to 1000 nm). The light is refracted at the particles, here one or more bubble walls, by this scattering of the light, light beams being scattered laterally out of the medium. The scattering causes the light beam to be visible also from the side.

Advantageously, the contour of the light spot is determined from outside the container and compared to stored data. Usually, the foaming beverages are filled into transparent glass or plastic bottles. The light beam which can be generated by a commercially available, in particular focusing laser within a performance range of only a few mw, can thus be directed onto the foam from outside the container. The measuring device which detects the contour of the light spot is thus also to be disposed outside the bottle.

To further increase the accuracy of the determination of the foam density, the density of the foam can be determined by means of several light beams, in particular light bundles. It is known that the density of the foam is not constant across its extension, so that errors can occur in case of a single measurement. The light beams are irradiated into the foam such that the formed light spots do not overlap and their contours can be clearly identified. As an alternative, differently pulsed lasers can also be employed by means of which even overlapping light spots can be identified and the density can be determined on their basis.

In addition, the light spots brought about by the light beams are determined by means of at least one measuring device. The measuring device is also used for determining the foam height in the beverage bottle, so that it already detects the complete foam height. With a measuring device, it is possible, depending on the orientation of the light beams, to detect several light spots and to determine the density in a respective area of the light beam. However, several light beams can also be oriented such that several measuring devices are required to detect all light spots.

By means of the liquid quantity detected in the foam in the process, thus the filling level to be expected in the container, or else in general the quality or density of foam, can be detected.

Accordingly, the measuring device is embodied such that it can detect the contour of a light spot generated in the foam by the light beam. For this, the device comprises a light source and a measuring device which are disposed in the area of the containers to be filled. The contour permits conclusions on the foam density whereby the density of the foam can be determined by simple means.

According to an advantageous further development of the disclosure, the measuring device, in particular a camera, is disposed laterally to the light beam input to measure the light spot from the side. The refraction brings about a scattering of the light beam whereby the light beam becomes visible in the foam laterally to its longitudinal axis. Depending on the resulting scattered ray from the foam density, the light spot varies with respect to outline, size and brightness on the foam. By means of the camera, the contour of the light beam or the outline of the scattered ray can be easily detected. That means, contour here means the reduction of the brightness from the center of the beam towards both sides transverse to the direction of the beam along the beam as well as the absolute brightness values. In a simplified evaluation, this would be for example the ratio of length to width of the outline of the scattered ray.

It is provided according to a further advantageous embodiment that the light beam is generated by a preferably pulsed laser or a similar focusing light source. A laser emits a sharp, bundled light beam which can lead to a good result in the contour measurement of the light spot even without any further optical bundling.

Advantageously, the laser can be triggered to the frequency of the camera. It is thus possible to not only take individual pictures of the foam, but also several subsequent pictures or a continuous picture in the form of a film.

According to a further advantageous embodiment of the disclosure, several light sources and measuring devices are disposed laterally of the container. Due to the varying foam density even in one single foam formation, it is useful for the accuracy of the measurement to dispose several light sources such that different areas of the foam can be measured. Advantageously, the light sources are then disposed here one upon the other along the height of the foam. As an alternative to this, the light sources can also be arranged in one plane, so that the foam is irradiated from two or more sides with one light bundle each. The camera is in contrast usually designed such that a larger area of the foam is detected, whereby it is possible to detect several light sources disposed one upon and/or next to the other and their generated light spots with one camera. To exactly determine the contour of the light spots, several light spots recorded in one picture are then separated.

The measuring device is disposed laterally and/or in parallel to the longitudinal axis of the light beam. As the light spot exits from the foam laterally to the longitudinal axis of the light beam, the measuring device is disposed laterally to the longitudinal axis of the light beam. Here, it is irrelevant whether the same is disposed to be oriented perpendicularly to the light beam. One only has to take care that the measuring device detects the light spot or the contour of the light spot invariably.

Advantageously, the device comprises a computer for calculating the liquid quantity bound in the foam by comparing stored data of the contour of the light spot measured by the measuring device.

According to a preferred further development, the computer comprises a memory in which data on the container and the liquid, in particular the dimension and material thickness of the container, preferably of the neck of the bottle, as well as the quality of the liquid can be stored. These data and information are collected and stored in the memory before the containers are filled. Due to the exogenous measurement, that means from outside the container, a curvature and the material thickness of the container wall influence the measurement of the light spot, which can then be taken into consideration in the determination of the result when the data are correspondingly stored in advance. Equally, by means of the measured height of the foam and the known volume of the container, one can determine the volume of the foam layer in this area. The computer comprises an image processing program for determining the contour of the light spot. The data provided by the camera are processed by the image processing program such that the exact size of the light spot can be determined, for example in a unit of area. The same also applies to the calculation of the foam height, which is possible with the image processing program, as well as the filling quantity. With an image processing program, one can thus draw conclusions on the foam density. In case of overlapping light spots or pictures taken subsequently, these can be also analyzed by means of the image processing program.

It is furthermore advantageously possible to integrate the device into existing camera devices for filling level controls. Existing camera systems which are already installed in filling systems for filling level control can be thus retrofitted within little time and at little effort.

BRIEF DESCRIPTION OF THE DRAWINGS

In the following, a preferred embodiment of the disclosure will be illustrated more in detail with reference to the drawing. In the drawings.

DETAILED DESCRIPTION

Figure 1:
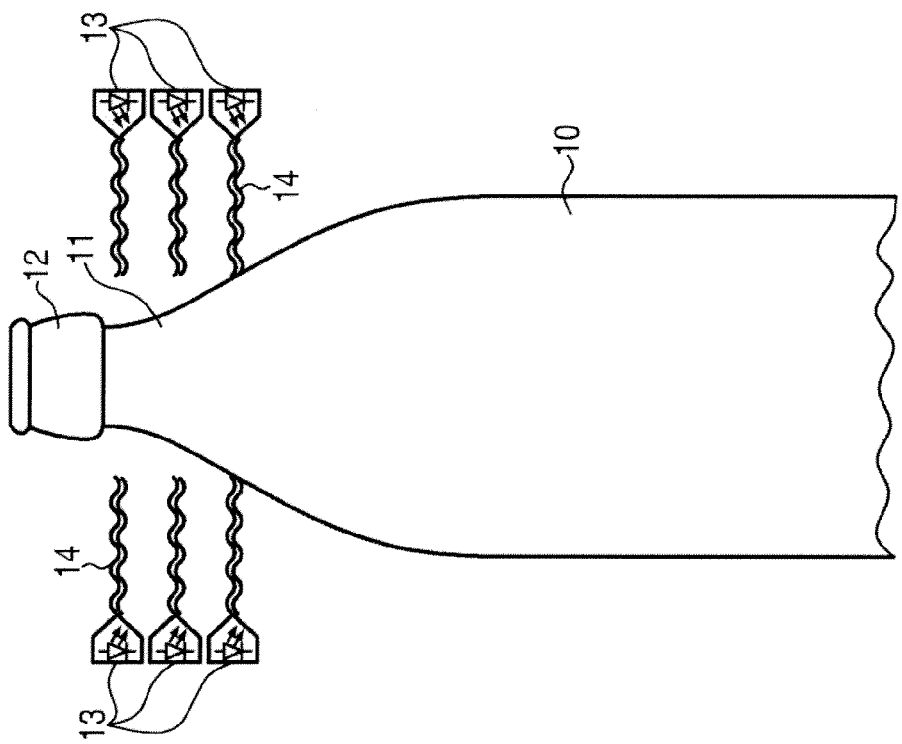
FIG. 1 shows a side view of an upper area of a beverage container with laterally disposed light sources.

In FIG. 1, an upper area of a beverage container is represented. This is a beverage bottle 10 with a conically tapering neck of the bottle 11. The neck of the bottle 11 ends in a thickening opening area 12. The beverage bottle 10 is a commercially available narrow-neck bottle as it is often employed in the beverage industry, in particular in the beer industry.

In the area of the neck of the bottle 11, several light sources in the form of lasers 13 are laterally disposed in the represented embodiment. Two lasers 13 each lie in one plane. Altogether, six lasers 13 are arranged in three planes arranged one upon the other. Thus, the neck of the bottle 11 is surrounded by lasers 13 at least in an area underneath the opening area 12, the lasers 13 being disposed along a longitudinal axis of the beverage bottle 12.

The lasers 13 which are disposed in one plane are positioned to be offset with respect to each other at the circumference. This means that the respectively emitted light bundles 14 of the lasers 13 do not extend axially with respect to each other. Their axes are rather located in the shown embodiment in the corresponding plane offset by ca. 120° with respect to each other. An arrangement of two lasers 13 arranged in one plane can be seen in FIG. 2.

Figure 2:
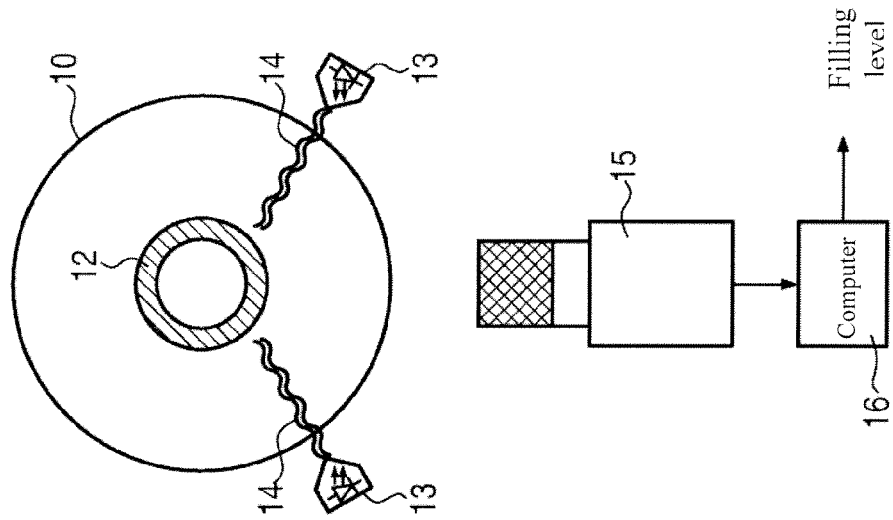
FIG. 2 shows a plan view onto the beverage container with laterally disposed light sources and a measuring device.

FIG. 2 shows a plan view onto the beverage bottle 10 with two laterally disposed lasers 13. In addition, a measuring device 15 in the form of a camera is disposed laterally with respect to the beverage bottle 10 in the plane of the two lasers 13. Usually, the measuring device 15 is positioned with respect to the beverage bottle 10 such that it covers the complete area of the neck of the bottle 11. This means that the planes of the lasers 13 arranged one upon the other are detected by means of a single measuring device 15. Accordingly, several lasers arranged in parallel with respect to each other one upon and next to the other are assigned to one measuring device 15. As an alternative to this, however, one measuring device 15 can be assigned to each laser 13 or to a plane with lasers 13.

In FIG. 2, a computer 16 is moreover represented which comprises a memory in which data on the beverage bottle 10 and the beverage can be stored. For the calculation, e.g. data on the dimension of the bottle 10, in particular the neck of the bottle, and the wall thickness of the bottle 10 are stored. Moreover, data on the beverage itself can be possibly stored to permit, by means of beverage properties, a more precise interpolation or extrapolation over the complete height and thus the preparation of a vertical density profile. The stored data can be based on experimental values, tests or previous measurements. Moreover, the computer comprises an image processing program. By means of the image processing program, the contour of the light spot 17a, 17b can be determined.

Figure 3:
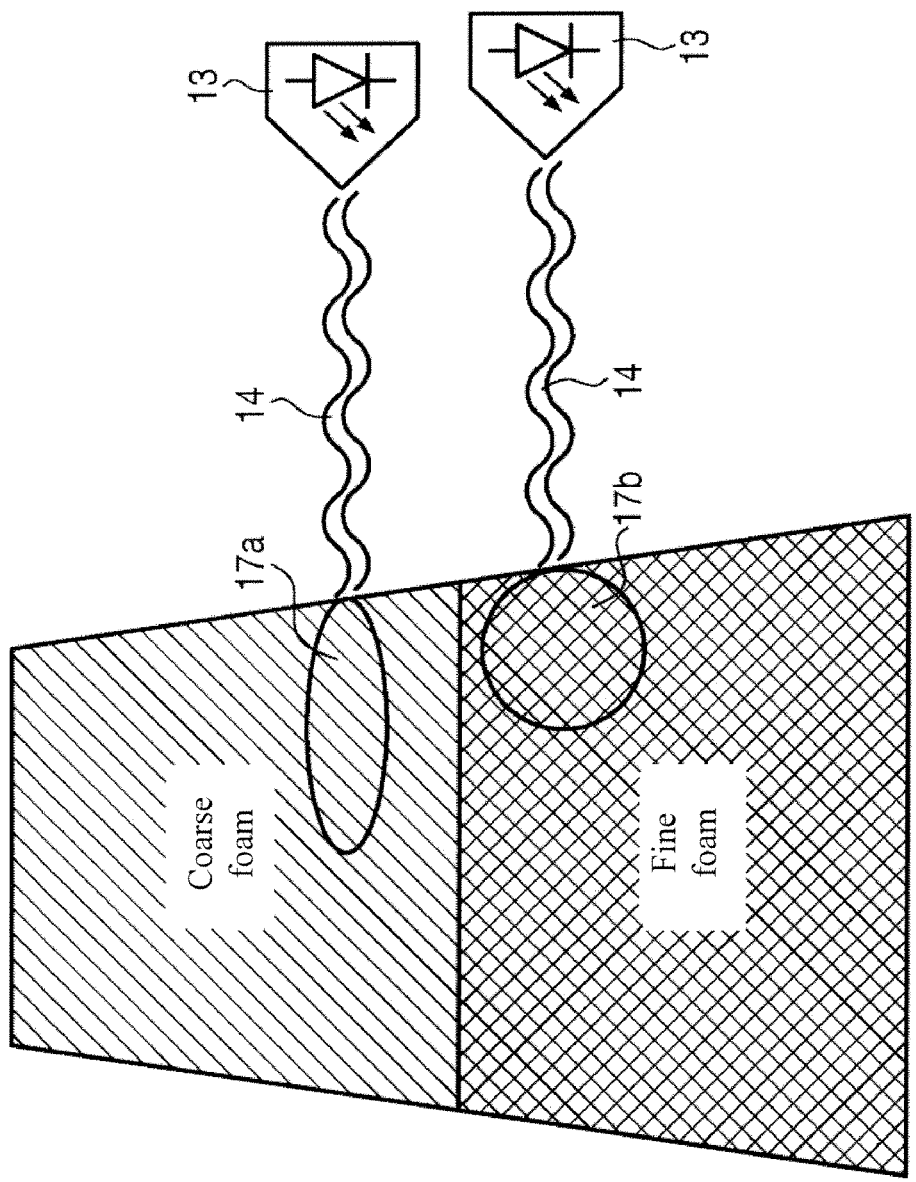
FIG. 3 shows a schematic diagram for explaining the disclosure.

Below, the method according to the disclosure will be illustrated more in detail with reference to FIG. 3: The foam layer formed in the area of the neck of the bottle 11 during filling contains a liquid quantity which, after the foam has settled, makes the level in the beverage bottle 10 rise. To be able to estimate which liquid quantity is bound in the foam already directly after filling, a beam of some μsec to a few msec is irradiated into the foam with the laterally disposed laser 13 which generates the light spot 17a or 17b, respectively, that can be identified from the side and has different contours depending on its density. The contour of this light spot is detected with the camera 15 positioned laterally with respect to the direction of the beam, and the liquid quantity is then determined from the measuring result, e.g. by comparison with previously collected data.

The measuring device 15 is usually designed such that, in addition to the detection of the light spots, it can also determine the height of the foam layer. This additionally permits to include several lasers disposed along the longitudinal extension of the beverage bottle 10 for determining the foam density. With a measuring device 15, thus a greater number of light spots projected onto the foam is possible. From the vertical foam density profile and the foam height, the liquid quantity stored in the foam can then be calculated by integration with the internal diameter being known.

It is usually sufficient to determine the foam density and thus the bound liquid quantity in a single measuring procedure. One measuring procedure corresponds to one picture of the camera. The laser/lasers are triggered such that their frequency corresponds to the recording time of the camera. As an alternative, several pictures of the light spots can be taken, for example to determine the chronological sequence of the settlement of the foam.

In a further application of the disclosure, the system according to the disclosure as control system in connection with HDE methods in the filling of oxygen-sensitive beverages is used to observe whether enough foam has been generated to press the residual oxygen out of the orifice.

The device can be easily integrated into existing filling level control means. As the filling level control is usually performed with a camera system already now, the disclosure can be easily realized because the existing system only has to be supplemented by the laser or lasers and a suited image processing program.

The invention claimed is:

1. Method for determining the foam density of foam, which is formed directly after a liquid has been filled into a container or before the subsequent closing of the container, comprising irradiating a light beam into the foam, and determining the contour of a light spot generated in the foam by the light beam, wherein the contour of the light spot is based on the degree of a scattering of the light beam in the foam, and the foam density is determined by using the contour of the light spot.

2. Method according to claim 1, and further comprising the step of determining the contour of the light spot from outside the container and comparing to stored data.

3. Method according to claim 1, and further comprising the step of determining the density of the foam by means of several light beams.

4. Method according to claim 3, and further comprising the step of determining the contour of light spots brought about by the light beams by means of at least one measuring device.

5. Method according to claim 3, wherein the several light beams are light bundles.

6. Device for determining the foam density of foam which is formed directly after a liquid has been filled into a container or before the container is subsequently closed, comprising a light source and a measuring device disposed laterally in the area of the containers, wherein the light source emits a light beam into the foam, and the measuring device detects the contour of a light spot generated in the foam by scattering of the light beam in the foam, the device further comprising a computer for calculating the foam density by using the contour of the light spot.

7. Device according to claim 6, wherein the measuring device is disposed laterally to an input of the light beam to measure the light spot from the side.

8. Device according to claim 7, wherein the measuring device is a camera.

9. Device according to claim 6, wherein the light beam is generated by one of a laser or a similarly focused light source.

10. Device according to claim 6, wherein several light sources and measuring devices are disposed laterally to the container.

11. Device according to claim 6, and a computer for calculating the liquid quantity bound in the foam by comparing stored data of the contour of the light spot measured by the measuring device.

12. Device according to claim 11, wherein the computer comprises a memory for storing data on the container and the liquid.

13. Device according to claim 12, wherein the data stored on the container is of the dimension and material thickness of the container.

14. Device according to claim 12, wherein the data stored in the container is of the neck of the container.

15. Device according to claim 12, wherein the data stored on the liquid is of a property of the liquid.

16. Device according to claim 6, and as installed into an existing camera filling level control device.

* * * * *